United States Patent [19]

Coleman

[11] Patent Number: 4,644,939
[45] Date of Patent: Feb. 24, 1987

[54] SHOULDER BRACE

[76] Inventor: Thomas A. Coleman, Meyers Rd., Shaftsbury, Vt. 05262

[21] Appl. No.: 699,829

[22] Filed: Feb. 8, 1985

[51] Int. Cl.[4] ............................ A61F 5/02; A61F 5/37
[52] U.S. Cl. ................................. 128/78; 2/45; 128/87 R
[58] Field of Search ............... 128/78, 87 R, DIG. 19; 2/44, 45

[56] References Cited

U.S. PATENT DOCUMENTS

| 95,235 | 9/1869 | Kent | 128/78 |
|---|---|---|---|
| 530,038 | 11/1894 | Gallegos . | |
| 559,024 | 4/1896 | Bessing | 2/45 |
| 634,429 | 10/1899 | Comly . | |
| 759,256 | 5/1904 | Ferneau | 128/78 |
| 1,129,515 | 2/1915 | Perry . | |
| 1,293,089 | 2/1919 | Hardy . | |
| 2,450,298 | 9/1948 | Peterson | 128/DIG. 19 |
| 2,859,746 | 3/1956 | Roberson . | |
| 3,499,441 | 3/1970 | Hall | 2/44 |
| 3,856,004 | 12/1974 | Cox . | |
| 3,906,944 | 9/1975 | Christen . | |
| 4,302,849 | 12/1981 | Margetson . | |

FOREIGN PATENT DOCUMENTS

| 182820 | 1/1955 | Austria | 128/DIG. 19 |
|---|---|---|---|
| 190631 | 8/1956 | Austria | 128/DIG. 19 |
| 231054 | 5/1910 | Fed. Rep. of Germany | 128/78 |
| 2140981 | 2/1973 | Fed. Rep. of Germany | 128/78 |
| 49636 | 5/1939 | France | 128/DIG. 19 |
| 560631 | 5/1956 | Italy | 2/45 |

OTHER PUBLICATIONS

Shoulder and Elbow Braces (Hohmann, G., Orthopadische Tecknike; Ferdinand Enke, Verlag Stuttgart, 1941, and Thorndike, A., Athletic Injuries, Prevention, Diagnosis, and Treatment; Lea and Febiger, Philadelphia, Pa., 1942).

Primary Examiner—Clyde I. Coughenour

[57] ABSTRACT

A shoulder brace having an elastic web that is anchored to provide tension to force and guide the humerus upward along its longitudinal axis into the glenoid fossa. The brace restricts elevation of the humerus and opposes both anterior and posterior rotation of the humerus. The brace provides a guided tension force to the humerus along its longitudinal axis, and that force is provided perpendicular to the medial (anterior/posterior) plane and circumferentially around (360°) the humerus axis. Specifically, the elastic web comprises a sleeve region and a shoulder region connected to the sleeve region. In use, the anchors tense the shoulder region inferiorly and medially and tense the sleeve region longitudinally along the arm away from the shoulder.

9 Claims, 3 Drawing Figures

SHOULDER BRACE

BACKGROUND OF THE INVENTION

This invention relates to appliances to prevent or aid healing of shoulder injuries.

Dislocation of the shoulder joint—i.e., separation of the head of the humerus from the glenoid fossa—involves injury to various soft tissue that must be immobilized to permit healing. In addition, such tissue may be susceptible to repeated injury, even after superficial healing is complete, if the tissue is not properly protected during exercise.

Currently, slings supported from the shoulder may be used in an attempt to support the arm and to immobilize the shoulder joint.

Christen, U.S. Pat. No. 3,906,944, discloses an appliance to restrict movement of the upper arm during periods of strenuous activity. The appliance includes a pad placed on top of one shoulder and extending slightly over the arm. One or two straps run over the top of the pad, around the user's body, and under the opposite armpit. The appliance restricts movement of the upper arm to less than 90 degrees away from the body. A portion of each strap is elasticized to pull the pad tightly against the shoulder and upper arm of the wearer.

Robertson, U.S. Pat. No. 2,859,746, discloses a shoulder brace that includes a rounded pad extending around the shoulder and under the armpit where it is fixed to a vest having suspender type straps to oppose elevation of the pad. The straps are adjustable to force the pad up into the armpit to provide supporting action. The pad moves vertically to provide support as the arm is raised.

Cox, U.S. Pat. No. 3,856,004, discloses a brace for support while a clavicle injury is healing. A fabric-covered foam strap extends around the shoulder and under each armpit to support the upper arm. The strap connects to straps running over each shoulder connecting to a Y-shaped coupler in the middle of the user's front and back. A circumferential strap around the user's body is also connected to each of the Y-shaped couplers.

Various other braces and supports are disclosed that include a vest. See, for example, Margetson, U.S. Pat. No. 4,302,849; Hardy, U.S. Pat. No. 1,293,089; Gallegos, U.S. Pat. No. 530,038; Comly, U.S. Pat. No. 634,429; and Perry, U.S. Pat. No. 1,129,515. In some cases (e.g. Hardy and Perry) these vests include stretchable or resilient fabric.

Blessing, U.S. Pat. No. 559,024, discloses a shoulder brace-chest expander with knit sleeves. An elastic strap extends around each shoulder and crosses in the back to pull the arms rearward. Each sleeve is connected to a chest piece, and the rear portions of those two chest pieces are connected with elastic material to provide an additional force drawing the arms rearward.

Hall, U.S. Pat. No. 3,499,441, discloses a brace for supporting a clavicle fracture. Sleeve segments are elastically connected across the middle of the chest and back.

SUMMARY OF THE INVENTION

In one aspect, the invention generally features a shoulder brace having an elastic web for the upper arm and shoulder with anchor means adapted to provide web tension to force and guide the humerus upward along its longitudinal axis into the glenoid fossa. The brace provides guided tension force to the humerus along its longitudinal axis into the glenoid fossa, and that force is provided perpendicular to the medial (anterior/posterior) plane and circumferentially around (360°) the humerus axis. Specifically, the elastic web comprises a first region around the upper arm sized and positioned to extend around the circumference of at least a portion of the user's deltoid-bicep region and extending to a second region over the top of the shoulder. Anchor means are provided so that, in use, the shoulder region is pulled inferiorly and medially, and the sleeve region is pulled longitudinally along the arm away from the shoulder, thereby tensing the web to create force circumferentially around the longitudinal axis of the humerus, guiding the humerus upward into the glenoid fossa thus restricting elevation of the humerus beyond horizontal and restricting anterior and posterior rotation of the humerus.

In preferred embodiments, the sleeve region is anchored at a plurality of points around its circumference and the shoulder region is anchored at a plurality of points over the top of the shoulder. An element extends under the axilla to connect anterior and posterior portions of the second web regions. Also in preferred embodiments, the anchor means for the second web region includes a horizontal belt below the user's rib cage, and a vertical member is connected to the belt and to the shoulder region of the web to provide inferior (downward) tension on the web. The brace includes a second elastic web for the user's other arm and shoulder that has elements corresponding to the first web, and the anchor includes a second vertical member, on the other side of the user's neck from the first vertical member, connected to the belt and to the second web, the two vertical members being attached by at least one anterior horizontal connector and one posterior horizontal connector. The anchor means for the second web region also includes a strap attached at one end to the top of the shoulder element of the web and at the other end to a horizontal member (e.g., to a connector between the vertical members or to the belt). The web is a woven, two-way stretch fabric.

The axial guiding force applied to the humerus is adequate to aid primary healing following dislocation and to reduce strain on a joint that is weakened, e.g., following injury to ligaments and muscles. The brace maintains a position that minimizes stress on and stretching of the shoulder ligaments and muscles. Specifically, the humerus is forced along its axis into the glenoid fossa. This upwardly and inwardly directed force is complemented by force directed downwardly on the top of the shoulder to oppose the humerus. Even with the arm relaxed, the upper arm is slightly elevated, not by a lever force around a fulcrum in the axilla, but by a force directed axially around the circumference of the humerus. Such an axial force avoids strain on soft tissue allowing the humerus to be elevated through a substantial angle (less than 90 degrees) without joint stress. In contrast, lever/fulcrum arrangements generally require that elevational movement of the humerus be more severely restricted. Finally, the brace opposes rotation of the humerus beyond a normal physiologic degree.

An individual needing appliance therapy following shoulder joint injury, or in the state of weakened joint functions, may wear the appliance in the first aspect during minimal or moderate joint activity.

Other features and advantages to the invention will be apparent from the following description of the preferred embodiment thereof and from the claims.

DESCRIPTION OF THE PREFERRED EMBODIMENT

I first briefly describe the drawings.

DRAWINGS

STRUCTURE OF BRACE

Figure 1:
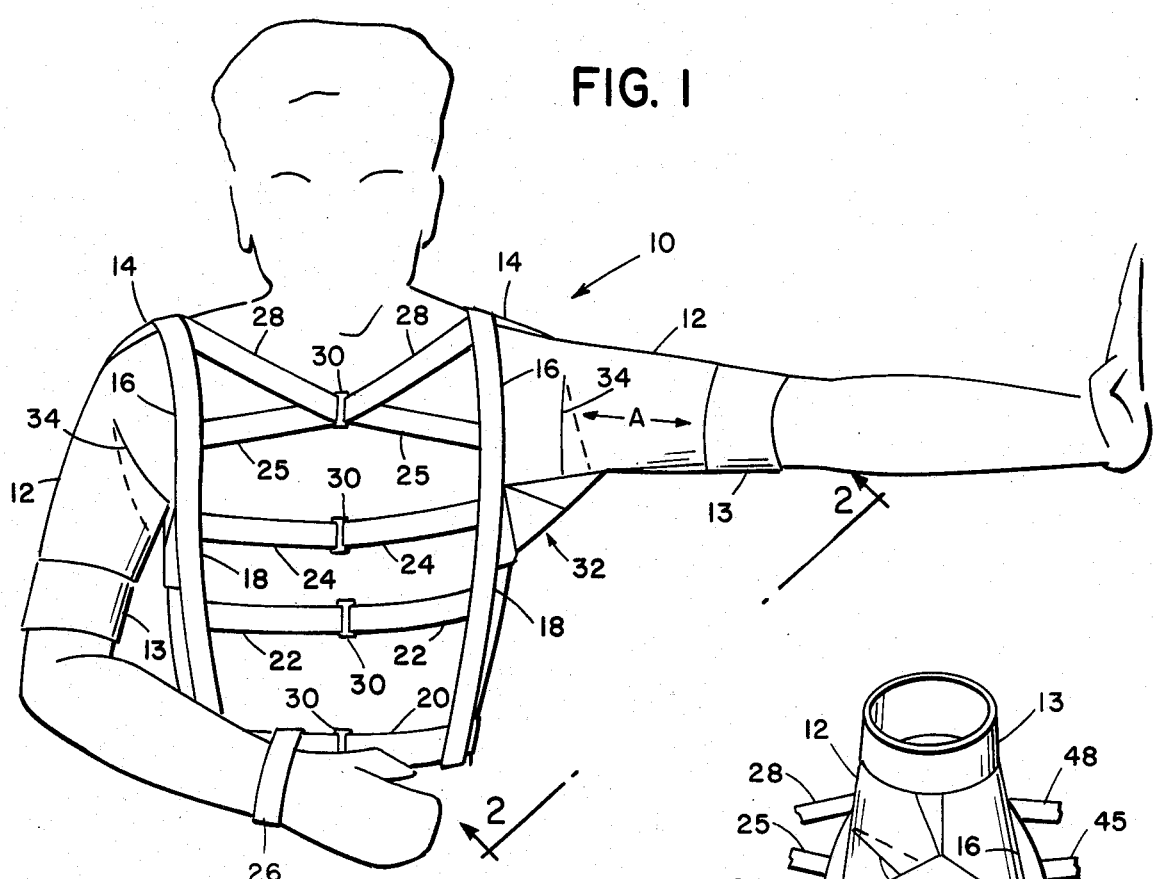
FIG. 1 is an anterior view of a user wearing the shoulder brace with maximum elevation of the right arm.
Figure 2:
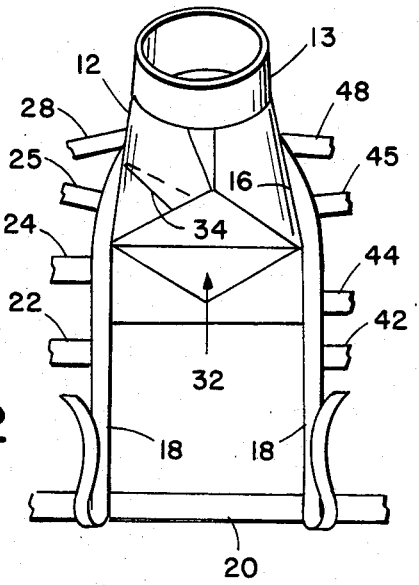
FIG. 2 is a side view taken along 2—2 of FIG. 1 with the user's outline omitted.

In FIG. 1, brace 10 has symmetrical right and left sides, only one of which will be discussed in detail. The brace includes a right sleeve portion 12 that surrounds the upper arm. The sleeve portion extends up the arm to a shoulder portion 14 extending over the shoulder anteriorly and posteriorly along the sides of the trunk. The shoulder portion terminates in a medial edge 16 that is attached to a strap 18 with generally vertical anterior and posterior segments. A horizontal belt 20 extends around the trunk and anchors one end of strap 18 in the front and the opposite end of strap 18 in the back. Under the arm are two triangles of elastic material sewn together to form a diamond 32. The diamond is connected by heavy cloth to strap 18 in the front and back as shown in FIG. 2.

Horizontal straps 22, 24, and 25 connect strap 18 to the corresponding strap on the opposite (left) side. A diagonal strap 28 extends from the apex of shoulder segment 14 to a D ring 30 on strap 25. Straps 18, 20, 22, 24, 25, and 28 anchor the elastic portion of the brace and maintain the desired tension in the elastic. The straps are canvas, and their length is adjusted by passing them through D rings and anchoring them with Velcro. Horizontal belt 20 provides resistance to upward movement of the brace. The diagonal belts provide a downward force to the brace as well as resistance to excessive anterior or posterior movement of the appliance, thus helping to guide the elastic force on the humerus. A wrist strap 26 can be fixed about the wrist and attached to belt 20 to support the lower arm for recent dislocants.

Figure 3:
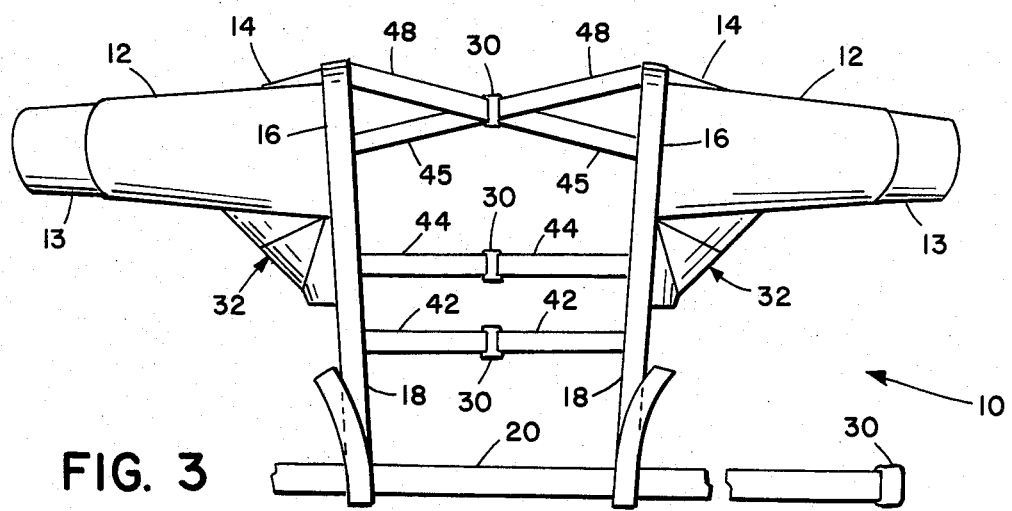
FIG. 3 is a posterior view of the brace of FIG. 1 with both arms elevated.

FIG. 3 shows a posterior view of the brace. The posterior construction is as shown for the anterior construction (except for the tuck 34 described below). Belts 42, 44, 45, and 48 correspond to belts 22, 24, 25, and 28, respectively.

CONSTRUCTION OF BRACE

The elastic portion of the brace is preferably an elastic material that has been woven to have a directional (e.g., 2-way) stretch as shown by arrow A in FIG. 1. For example, two-way orthopedic stretch fabric obtained from Finer Brothers, Mineola, N.Y., may be used. The brace is constructed by sewing together the various parts shown in the figure using conventional techniques.

OPERATION OF BRACE

Tension is created by an elastic cuff 13 to secure the lower end of the sleeve around the arm (e.g., a 3" cuff). The shoulder and upper sleeve are tensioned by the anchoring straps and the user's body to create a force on the humerus guiding it upward along the humerus and into the glenoid fossa. That axial force is spaced circumferentially around the shoulder joint so as to avoid non-physiologic rotation or displacement of the humerus. Specifically, the tension provided by the stretch fabric and the fabric anchoring system provides a force that allows the humerus to pivot during elevation about a stationary point P overlying the glenoid fossa. Thus rotational bias is avoided not only with the arm at rest but also as the arm is elevated. And even at rest, the appliance generates the above-described axial force so that the weight of the resting arm does not strain the shoulder joint. More specifically, the force generated is symmetric about the axis of elevation—i.e., the vertical plane through which the arm moves during elevation without rotation. The force along axis A is complemented by a force directed downwardly on the top of the shoulder to oppose movement of the humerus.

The wearer can put on the brace by inserting each of his arms into a respective sleeve portion and adjusting the horizontal and diagonal belts. Once on, the brace allows remarkable freedom of movement while maintaining proper positioning of the humerus in the shoulder joint and thus preventing additional trauma to soft tissue injured by the shoulder dislocation. FIG. 1 demonstrates the freedom to elevate the arm up to 90 degrees. Movement beyond 90 degrees is substantially limited by the elastic force. Similarly, the appliance controls the degree of posterior rotation of the shoulder joint, but generating restoring forces.

If desired, the elastic may be tucked near the joint to control the amount of anterior or posterior movement. For example, a tuck 34 in the anterior portion of the shoulder section to allow more anterior and less posterior motion.

In the early stages of therapy, it may be desirable to support the lower arm by placing the wrist in cuff 26 and attaching the cuff to belt 20.

The upward and inward guiding forces reduces strain on injured soft tissue, aids healing, and dissipates forces that could reinjure the tissue.

Other embodiments are within the following claims. For example, the positioning of the cross-straps of brace 10 may be modified to accommodate a female user, e.g. by moving strap 24 upward.

I claim:

1. A shoulder brace for treating a dislocated shoulder, said brace being effective to force the humerus into the glenoid fossa, said brace comprising:

(a) a web having a first web region sized and positioned to extend around the circumference of at least a portion of the deltoid-bicep region of the upper arm of a user, a second web region extending along the arm from the first web region toward a third web region sized and positioned to extend over the top of the shoulder of the user, each said web region comprising two-way stretch elastic; and (b) a first anchor attached to said third web region and extending therefrom across the chest, and a second anchor attached to the rear of said third web region and extending therefrom across the users back, said anchors being adapted in use to apply tension to said web to pull said first web region away from said third region and to pull both anterior and posterior portions of said third web region inferiorly and medially, thereby creating force circumferentially around the longitudinal axis of the humerus guiding the humerus upward into the glenoid fossa, thus restricting elevation of the humerus beyond horizontal and restricting anterior and posterior rotation of the humerus.

2. The brace of claim 1 wherein said first web region is anchored at a plurality of points around its circumference, and said third web region is anchored at a plurality of points over the top of the shoulder.

3. The brace of claim 1 wherein said third web region includes an anterior portion and a posterior portion, said brace comprises an axilla element extending under the axilla and connecting said anterior portion to said posterior portion.

4. The brace of claim 1 wherein said first anchor comprises a vertical member attached at a plurality of points along the front edge of said third web region, and said second anchor comprising a vertical member attached at a plurality of points along the rear edge of said third web region, each said vertical member being attached to a horizontal belt that is sized and positioned to extend about the user's torso below the rib cage to provide downward tension on said web.

5. The brace of claim 4 wherein said vertical members comprise a continuous member extending over the user's shoulder and said first and second anchors further comprise a second continuous member extending vertically on the users' chest, over the user's neck on the opposite side thereof from said first continuous member, and vertically down the user's back, said second continuous member being, attached to said first continuous member by at least one anterior horizontal connector and at least one posterior vertical connector, said second continous member being attached to said horizontal belt.

6. The brace of claim 5 corprising a second elastic web sized for the user's other arm and shoulder, respectively, said second continuous member being attached to said second web.

7. The brace of claim 4 wherein said brace further comprises a diagonal strap attached at one end, to said third region of said web at the top of the shoulder and at the other end to one of said anchors.

8. The brace of claim 1 wherein each said web region comprises orthopedic elastic.

9. The brace of claim 1 wherein said anchors are positioned to tense said elastic web to provide a force to the humerus circumferentially around the humerus axis and symmetric tothe vertical plan through which the arm moves when it is elevated without rotation.

* * * * *